a12) United States Patent
Miller et al.

(10) Patent No.: US 7,803,320 B2
(45) Date of Patent: Sep. 28, 2010

(54) APPARATUS FOR QUALITY CONTROL ANALYSIS OF AN ON-SITE PREPARED PHARMACEUTICAL PRODUCT

(75) Inventors: Peter Miller, New London, CT (US); Andrew M. Leach, Clifton Park, NY (US); Eric Telfeyan, Guilderland, NY (US); David B. Whitt, Albany, NY (US)

(73) Assignee: General Electric Company, Niskayuna, NY (US)

( * ) Notice: Subject to any disclaimer, the term of this patent is extended or adjusted under 35 U.S.C. 154(b) by 401 days.

(21) Appl. No.: 11/747,769

(22) Filed: May 11, 2007

(65) Prior Publication Data

US 2008/0279723 A1 Nov. 13, 2008

(51) Int. Cl.
*G01N 21/00* (2006.01)
*G01N 31/00* (2006.01)

(52) U.S. Cl. .................. 422/58; 422/62; 422/68.1; 422/82.05; 422/100; 206/569; 206/571

(58) Field of Classification Search ............ 422/58, 422/62, 68.1, 82.05, 100; 206/569, 571; 210/656, 635
See application file for complete search history.

(56) References Cited

U.S. PATENT DOCUMENTS 5,496,301 A 3/1996 Hlavinka et al.
6,685,875 B2 2/2004 Usui et al.
2002/0144949 A1 10/2002 Berger et al.
2004/0247489 A1* 12/2004 Fernando et al. ............ 422/100
2004/0265177 A1* 12/2004 Nicoli et al. ................. 422/73
2005/0242115 A1 11/2005 Gaeta et al.
2007/0041875 A1 2/2007 Bach et al.
2007/0062934 A1* 3/2007 King .......................... 219/679

OTHER PUBLICATIONS

PCT Search Report-Aug. 5, 2008.

* cited by examiner

*Primary Examiner*—Jill Warden
*Assistant Examiner*—Dean Kwak
(74) *Attorney, Agent, or Firm*—Eileen W. Gallagher (57) ABSTRACT

A quality control system for measuring parameters in a pharmaceutical product includes a receiver vessel to receive a pharmaceutical product therein. The quality control system also includes a sample tube having a first end attached to the receiver vessel to remove pharmaceutical product from the receiver vessel and an appendage connected to a second end of the sample tube. The appendage includes at least one chamber therein to receive a quantity of pharmaceutical product from the receiver vessel. A valve positioned within the sample tube controls flow of the pharmaceutical product to the appendage and prevents flow of the pharmaceutical product from the appendage back into the receiver vessel. The system also includes a quality control device configured to measure at least one parameter of the pharmaceutical product in at least one of the receiver vessel and the appendage.

16 Claims, 5 Drawing Sheets

APPARATUS FOR QUALITY CONTROL ANALYSIS OF AN ON-SITE PREPARED PHARMACEUTICAL PRODUCT

BACKGROUND OF THE INVENTION

The present invention relates generally to a method and apparatus for performing multiple quality control (QC) measurements on a pharmaceutical product and, more particularly, to a method and apparatus for performing rapid QC measurements of an on-site or point-of-use prepared pharmaceutical product.

Quality control analysis of pharmaceutical products is an essential task that helps to ensure the safety of products used in the field of health care and eliminate the risk of an out of specification product making its way into a patient. Historically the quality of these pharmaceutical products has been measured by the manufacturer of the product prior to shipment to an end destination. For example, a manufacturer will perform a QC analysis of a parenteral solution after it has been packaged and sealed into a vial/vessel to ensure the quality thereof before shipment to a health care provider. Thus, the pharmaceutical product is considered safe for medical use until its expiration date without any further QC analysis required by the health care provider, assuming proper storage and handling.

With the development of pharmaceutical products whose final preparation occurs immediately prior to injection, QC analysis performed by a manufacturer before shipment of the product is not an option. Thus, to ensure the validity of pharmaceutical products prepared in such a manner, QC analysis must occur on-site where the pharmaceutical product is being prepared for injection into the patient. Such QC analysis must not only be performed accurately and efficiently, but the sterility of the prepared pharmaceutical product must also be ensured.

One example of a pharmaceutical product whose final preparation occurs immediately prior to injection is a hyperpolarized imaging agent (e.g., $^{13}C_1$-pyruvate) for use in MRI and NMR spectroscopy. Hyperpolarizing of an imaging agent for use in MRI and NMR spectroscopy is done to increase sensitivity in the imaging agent; however, such hyperpolarizing can only be performed immediately prior to injection of the imaging agent into a patient, as the hyperpolarized imaging agent has a very short life span. That is, the imaging agent must be quickly transferred from its production source to its place of intended end use (i.e., injection into a patient) within a matter of minutes. For such a product, QC analysis performed immediately prior to injection is the only option.

The actual QC analysis of the pharmaceutical product can be performed in either a contact or non-contact manner. While a non-contact QC measurement method reduces the chance of contaminants being introduced into the product, such a QC measurement method is not always possible. That is, the existence of applicable methods, cost considerations, and/or the design of a receiver vessel in which the product is located may not allow for non-contact measurement and may necessitate the use of a contact method for performing QC analysis. Regardless of the exact method used, efficacy and safety requirements must be met in performing the QC measurements.

Therefore, a need exists for an apparatus that allows for accurate and efficient QC analysis of a pharmaceutical product whose final preparation occurs just prior to injection into a patient. The apparatus should also allow for both contact and non-contact QC measurements of the pharmaceutical product and meet efficacy and safety requirements regardless of the type of QC analysis performed.

BRIEF DESCRIPTION OF THE INVENTION

The present invention overcomes the aforementioned problems by providing a quality control system for performing multiple quality control (QC) measurements on an on-site or point-of-use prepared pharmaceutical product.

In accordance with one aspect of the invention, a quality control system for measuring parameters in a pharmaceutical product includes a receiver vessel to receive a pharmaceutical product therein and a sample tube having a first end attached to the receiver vessel, the sample tube configured to remove pharmaceutical product from the receiver vessel. The quality control system also includes an appendage connected to a second end of the sample tube that has at least one chamber therein to receive a quantity of pharmaceutical product from the receiver vessel. A valve is positioned within the sample tube to control flow of the pharmaceutical product to the appendage and prevent flow of the pharmaceutical product from the appendage back into the receiver vessel. The quality control system further includes a quality control device configured to measure at least one parameter of the pharmaceutical product in at least one of the receiver vessel and the appendage.

In accordance with another aspect of the invention, a sterile fluid path system includes a vial constructed to contain a solidified pharmaceutical sample therein, a container having a dissolution medium therein to dissolve the solidified pharmaceutical sample, and a tubing system connecting the vial and the container configured to transfer the dissolution medium into the vial and transfer a pharmaceutical product out of the vial, wherein the pharmaceutical product is comprised of the dissolved solidified pharmaceutical sample and the dissolution medium. The sterile fluid path system also includes a receiver vessel attached to the tubing system to receive the pharmaceutical product and an appendage fluidly connected to the receiver vessel and having one or more isolated sections therein to receive a quantity of the pharmaceutical product. The sterile fluid path system further includes a one-way valve and tube assembly positioned between the receiver vessel and the appendage to control flow of the pharmaceutical product to the appendage and a measurement apparatus configured to measure at least one parameter of the pharmaceutical product in the appendage.

In accordance with yet another aspect of the invention, a method of constructing a quality control system for measuring parameters in a pharmaceutical product includes the steps of forming a receiver vessel configured to hold a liquid pharmaceutical product therein and fluidly connecting an appendage to the receiver vessel, the appendage having at least one chamber therein to receive the pharmaceutical product transferred thereto from the receiver vessel. The method also includes the steps of connecting a sample path to the receiver vessel and the appendage, positioning a one-way sterile valve in a sample path to control flow of the pharmaceutical product, and positioning a quality control device in proximity to the receiver vessel and the appendage to perform quality control measurements on the pharmaceutical product.

Various other features and advantages of the present invention will be made apparent from the following detailed description and the drawings.

BRIEF DESCRIPTION OF THE DRAWINGS

The drawings illustrate an embodiment presently contemplated for carrying out the invention.

In the drawings.

DETAILED DESCRIPTION OF THE INVENTION

Figure 1:
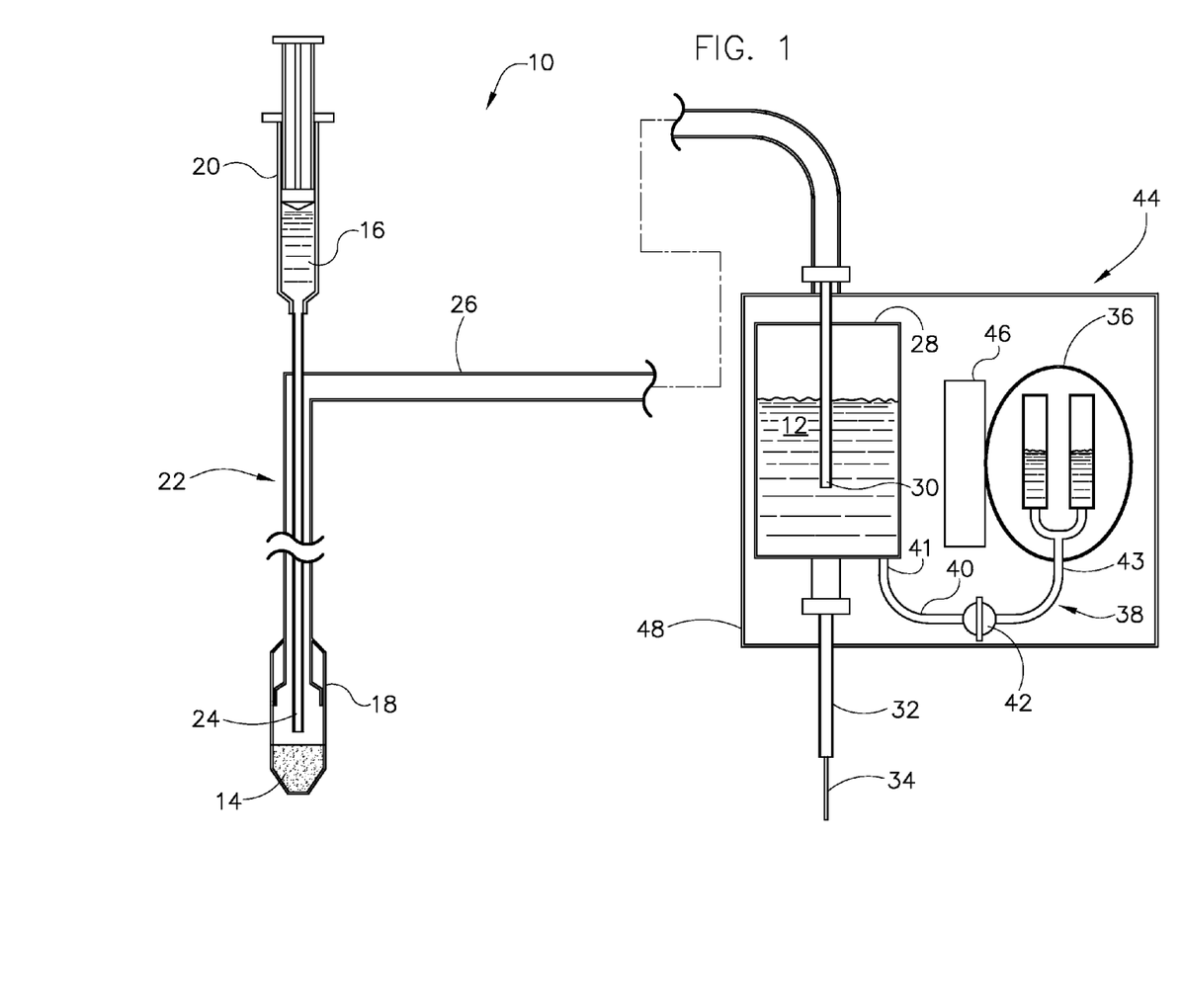
FIG. 1 is a block diagram and schematic of a fluid path system according to an embodiment of the current invention.

Referring to FIG. 1, a fluid path system 10 (i.e., fluid delivery system) is shown for dissolution, transport, and quality control (QC) analysis of a pharmaceutical product. In one embodiment, this pharmaceutical product 12 is a hyperpolarized solution for use as an imaging agent in magnetic resonance imaging (MRI) and NMR spectroscopy. The pharmaceutical product 12 is formed from a mixture of solid hyperpolarized material 14 (e.g., $^{13}C_1$-pyruvic acid) and dissolution medium 16. The fluid path system 10 can be made from medical grade materials if used in a clinical setting for preparing and delivering a parenteral solution to patients. Such materials are known and are generally plastics of validated quality in terms of leachables and stability. The materials for the fluid path system 10 are further selected on the basis of their thermal, mechanical, and chemical properties to be compatible with the product and environment (cryogenic and superheated temperatures, as well as high pressures). The fluid path system 10 is designed to provide a sterile barrier to the material and resulting pharmaceutical product 12 and all assemblies and parts therein are designed to prevent the user from unintentionally breaking the barrier. It is further envisioned that the fluid path system 10 can be made as a disposable part (i.e., single use), but can also be re-cycled completely or in part. A single use fluid path system ensures the maximum provision for sterility and patient safety.

The solid hyperpolarized material 14 is contained in a vial 18 (i.e., sample container), which is formed of a material that is non-reactive to the sample and to other commonly used solvents or solutions that might be used to dissolve the solid hyperpolarized material 14. The vial 18 can be formed of glass or another suitable material that would not react with the solid hyperpolarized material 14 or dissolution medium 16. A specified quantity or dosage of solid hyperpolarized material 14 is included in vial 18 to be mixed with the dissolution medium 16 and ultimately injected into a patient. Typically, this quantity/dosage of solid hyperpolarized material 14 will be around 2 ml in volume, although the exact quantity will be determined by qualified personnel.

In operation, the fluid path system 10 is used to dissolve the material 14 by way of dissolution medium 16 and transport the resulting pharmaceutical product 12 to a desired end location, where it is injected into a patient. To provide dissolution medium 16 for dissolving solid hyperpolarized material 14 in vial 18, a container 20 is included in the fluid path system 10. In one embodiment, the container 20 is a syringe that can be in the form of a motor powered or pneumatic syringe that produces force to inject dissolution medium 16 into fluid path system 10. Dissolution medium 16 therein is in a heated state to melt and dissolve the material 14 when mixed therewith. The dissolution medium 16 includes a basic solvent, such as sodium hydroxide, for neutralizing the material 14 and also possibly an ion chelator (e.g., EDTA). The dissolution medium 16 also includes therein a buffering agent, which commonly is in the form of a buffering salt such as TRIS, although other known buffering salts can also be used. While the dissolution medium 16 listed above is set forth as being composed of sodium hydroxide, EDTA, and TRIS, it is also envisioned that water or other solutions could be used instead.

Attached to vial 18 and container 20 is a tubing system 22 that forms a fluid path therebetween. Tubing system 22 is configured to transfer dissolution medium 16 from container 20 into vial 18 to dissolve material 14. Tubing system is also configured to remove pharmaceutical product 12 from vial 18 that results from the mixture of dissolved material 14 and dissolution medium 16, and transport the pharmaceutical product 12 to an end use location. In one embodiment, tubing system includes an inner tube 24 extending from container 20 down into vial 18 to transport dissolution medium 16. An outer tube 26 is sealed to vial 18 to allow for removal of the pharmaceutical product 12 therefrom. That is, as more dissolution medium 16 is injected into inner tube 24 and down into vial 18 to dissolve material 14, the quantity of pharmaceutical product 12 increases and is forced out of vial 18. The pharmaceutical product 12 thus flows up into outer tube 26 and is transported therethrough.

The pharmaceutical product 12 flows through tubing system 22 and eventually into a receiver vessel 28, where it collects until the desired amount of pharmaceutical product 12 has been collected. Tubing system 22 can be integrally connected to, or separately fitted on, receiver vessel 28 and can also include a nozzle 30 on the end thereof that extends down into receiver vessel 28. Nozzle 30 extends down into the interior of receiver vessel 28 and helps to ensure adequate mixing of pharmaceutical product 12 as it is transferred into the receiver vessel 28. That is, nozzle 30 provides for improved homogenization of pharmaceutical product 12 by mixing the solution as it is forced into the receiver vessel 28. The mixing produced by nozzle 30 also results in a greater surface area of the pharmaceutical product 12 being exposed, which enables a reduction in temperature to occur before injection of the pharmaceutical product into a patient. Receiver vessel 28 also contains an outlet port 32 to which a pharmaceutical giver set 34 may be connected after pharmaceutical product 12 has passed all QC tests. The giver set 34 enables the transfer of the pharmaceutical product from the receiver vessel to its end use.

Once the desired amount of pharmaceutical product 12 has been collected in receiver vessel 28, and before injection of the pharmaceutical product 12 into a patient, QC measurements are performed on the pharmaceutical product to determine its sterility and integrity. Multiple parameters can be measured in pharmaceutical product 12 and these include: temperature, pH level, mass, volume, liquid state polarization, and concentration. Other parameters not listed herein are also envisioned as being measured, and these parameters are determined, in part, by the pharmaceutical product 12 that has been prepared. To allow for various types of contact and non-contact QC measurements to be performed on pharmaceutical product 12, an appendage 36 is attached to receiver vessel 28. Fluidly connecting the receiver vessel 28 to appendage 36 is a valve and tube assembly 38. Valve and tube assembly 38 includes a sample tube 40 having a first end 41 connected to receiver vessel 28 and a second end 43 connected to appendage 36. Valve and tube assembly 38 also includes a one-way sterile valve 42 positioned within sample tube 40 configured to allow flow of pharmaceutical product 12 therethrough in only one direction, that being a flow from the receiver vessel 28 into appendage 36. That is, valve 42 blocks flow of pharmaceutical product 12 from appendage 36 back into receiver vessel 28, along with any other substances that may be present in appendage 36 for purposes of performing the QC measurements. One-way sterile valve 42 thus helps to ensure sterility of pharmaceutical product 12 contained in receiver vessel 28 and prevent any possible contaminants from entering into the receiver vessel 28 that might be introduced into the pharmaceutical product 12 by way of flow-back from appendage 36. While a one-way valve 42 has been described as being positioned in sample tube 40, it is also envisioned that a sterile filter could additionally be included along with the valve. The filter would aid in maintaining sterility in pharmaceutical product 12.

Receiver vessel 28 and appendage 36 form part of a quality control system 44 that allows for the QC measurements to be performed on pharmaceutical product 12. The overall quality control system 44 also includes a quality control device 46 to perform the actual QC measurements and analysis of the pharmaceutical product 12 and provide resulting data to an operator. Quality control device 46 can encompass/include a number of different contact and non-contact measurement devices (e.g., spectrometer, infrared pyrometer, probe, etc.) and processing components (i.e., CPU) therein for performing QC analysis, as will be explained in greater detail below. Quality control system 44 is enclosed in a housing 48 configured to position the receiver vessel 28 and appendage 36 to allow for QC measurements to be performed. Although shown as a single housing 48 in FIG. 1, it is also envisioned that quality control system 44 could include multiple housings that separately position receiver vessel 28 and appendage 36 for QC analysis.

Figure 2:
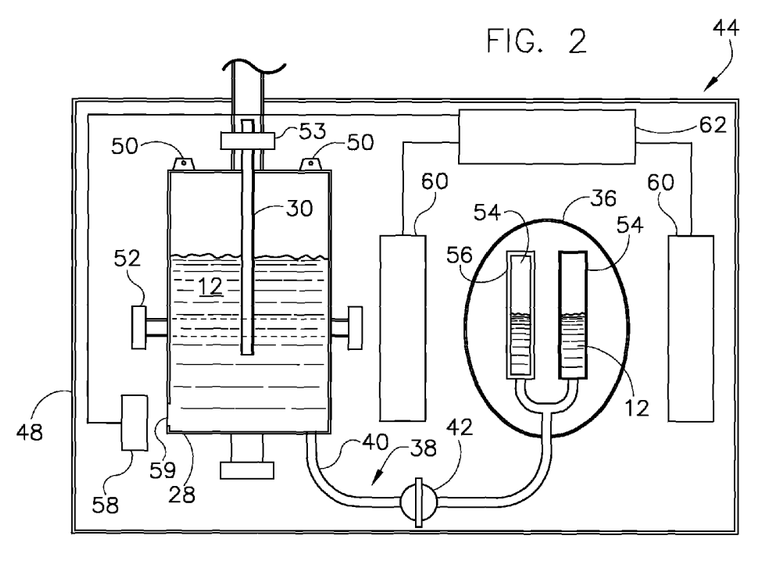
FIG. 2 is a cross-sectional view of a quality control system according to an embodiment of the current invention.

Referring now to FIG. 2, quality control system 44 is shown in greater detail. As stated above, a housing 48 aids in positioning the receiver vessel 28 and appendage 36. Housing 48 includes therein a hanger/balance arrangement 50 to which receiver vessel 28 can be attached. In one embodiment, receiver vessel 28 is a standard intravenous (IV) bag that is well known in the art, and the IV bag 28 is hung from hanger/balance arrangement 50. To transfer pharmaceutical product 12 from IV bag 28 to appendage 36, pressure is applied to IV bag by an automated displacement mechanism 52. The automated displacement mechanism 52 squeezes IV bag 28 to apply the pressure required for the transfer of pharmaceutical product 12 to appendage 36. Automated displacement mechanism 52 can take the form of a clamp or any other device suitable for applying variable levels of pressure to the IV bag 28 without rupturing the bag. Incorporation of any moving parts into automated displacement mechanism 52 for applying the pressure to displace pharmaceutical product 12 allows for use of a standard IV bag as the receiver vessel 28. Thus, the cost and complexity of receiver vessel 28 is reduced. A valve 53, which is a one-way valve or a closable valve, is also included in receiver vessel 28 and is positioned on nozzle 30 to prevent pharmaceutical product 12 from traveling back up the nozzle 30 when automated displacement mechanism 52 squeezes receiver vessel 28 to displace pharmaceutical product 12.

As pharmaceutical product 12 is forced out from receiver vessel 28 and through valve/tube assembly 38, it is collected in isolated sections 54 (i.e., chambers) within appendage 36. As shown in FIG. 2, appendage 36 contains two chambers 54 therein. It is also envisioned that a greater or lesser number of chambers 54 could also be used. The exact number and size of the chambers, as well as the overall construction of the appendage (i.e., material composition of the appendage), is determined by the analytical techniques used to perform the QC measurements.

In one method for QC analysis of pharmaceutical product 12, one or more active agents 56 (i.e., chemical reagents) are used that interact with the pharmaceutical product 12. In the case where a chemical reagent 56 is being used in the QC analysis, one or more chambers 54 in appendage 36 will be pre-treated with the chemical reagent. The chemical reagent 56 may be an indicator or some other type of compound that reacts specifically, in a measurable way, to the QC parameter(s) being measured. The pre-treatment of the chamber 54 may be done by: pre-filling part of the chamber with the reagent 56, coating one or more walls of the chamber with reagent, drying reagent in the chamber, or printing the reagent onto one or more of the chamber walls. When the pharmaceutical product 12 from receiver vessel 28 is introduced into chamber 54, the pharmaceutical product 12 and the chemical reagent 56 interact and the quality control device 44 measures a change induced by the interaction proportional to the parameter of interest. For example, a fluorescent pH indicator 56 may be deposited in one or more of chambers 54, and when the appendage is filled with pharmaceutical product 12, the pH indicator 56 will interact with the product 12 and produce a response that may be measured using fluorescence spectrometry.

Quality control system 44 also includes several components for performing optically based QC measurements on pharmaceutical product 12, generally identified as quality control device 46 in FIG. 1. Referring to FIG. 2, one of these components is an infrared (IR) pyrometer 58 positioned adjacent to receiver vessel 28 to measure the temperature of pharmaceutical product 12 therein. Receiver vessel 28 includes at least one thin wall 59 having a low thermal mass, which allows for optical measurements by way of the IR pyrometer 58. By measuring the amount of infrared radiation emitted from pharmaceutical product 12, the IR pyrometer 58 is able to rapidly obtain an accurate measure of the product's temperature. In determining temperature of the pharmaceutical product 12, quality control device 44 can also be calibrated to correct for changes in ambient conditions or any offsets that may be due to the receiver vessel 28 itself.

Another component included in quality control system 44 is a fiber optics based spectrometer system 60 that performs optical QC measurements on the pharmaceutical product 12 in appendage 36. Spectrometer 60 can, for example, determine a pH level in pharmaceutical product 12 by optically measuring via fluorescence spectrometry a luminescent reaction between fluorescent pH indicator 56 and pharmaceutical product 12.

A central processing unit (CPU) 62 is also included in quality control system 44 to evaluate the QC measurements gathered by the IR pyrometer 58, spectrometer 60, and by any other measurement devices present, to compare the measured values obtained for each parameter to a specified allowable range of values for each parameter. These values can be programmed into the CPU 62 by an operator, stored in the CPU's memory, or communicated to the CPU by another means familiar to one skilled in the art. The results of the measurements performed by the quality control system 44 will be compared to these set reference values and a pass/fail decision will be made on the safety and efficacy of pharmaceutical product 12.

Figure 3:
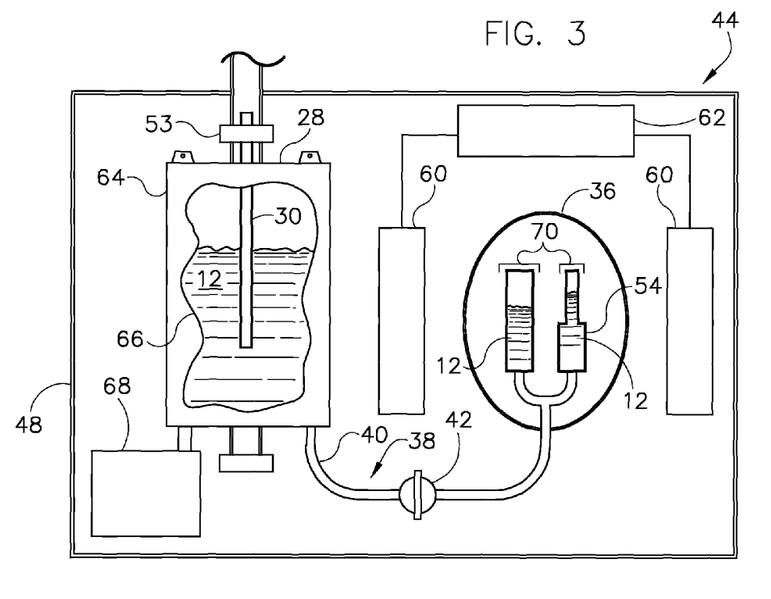
FIG. 3 is a cross-sectional view of a quality control system according to another embodiment of the current invention.

Another embodiment of quality control system 44 is shown in FIG. 3, wherein receiver vessel 28 is in the form of a rigid container 64 having a bladder 66 positioned therein. Bladder 66 includes pharmaceutical product 12 therein and an automated displacement mechanism is attached to rigid container 64 in the form of a pump 68. Pump 68 fills the space between rigid container 64 and bladder 66 with a pressurized gas or liquid in order to squeeze bladder 66 and force the flow of pharmaceutical product 12 out from receiver vessel 28 and into appendage 36. Such a configuration allows for the use of a fluid or gas to displace the product 12 without compromising the sterility of the quality control system 44. Additionally, the gas or fluid used to squeeze bladder 66 may be maintained at a specific temperature and aid in modifying the temperature of pharmaceutical product 12 in receiver vessel 28. A closable/one-way valve 53 is also included in receiver vessel 28 and is positioned on nozzle 30 to prevent pharmaceutical product 12 from traveling back up the nozzle 30 when bladder 66 is squeezed to displace pharmaceutical product 12.

As shown in FIG. 3, pharmaceutical product 12 enters into chambers 54 of appendage 36 to allow for QC analysis of the product. Appendage 36 is composed of a material that possesses optical properties suitable for non-contact optical measurements of the pharmaceutical product 12 therein. Chambers 54 in appendage 36 are designed to have a specified path-length 70 to allow for optical measurement of a specific property in pharmaceutical product 12. The chambers 54 are composed of plastic, glass or optical-grade quartz to allow for these optical measurements. If multiple optical properties are to be measured in pharmaceutical product 12, each chamber 54 can be designed to have a different path-length. Alternatively, it is also envisioned that each individual chamber 54 could include multiple path-lengths therein, where each unique path-length allows for separate optical QC measurements to be performed. For example, the concentration of components in pharmaceutical product 12 in chambers 54 may be determined by absorbance measurements through fixed path-lengths designed into chambers 54.

Figure 4:
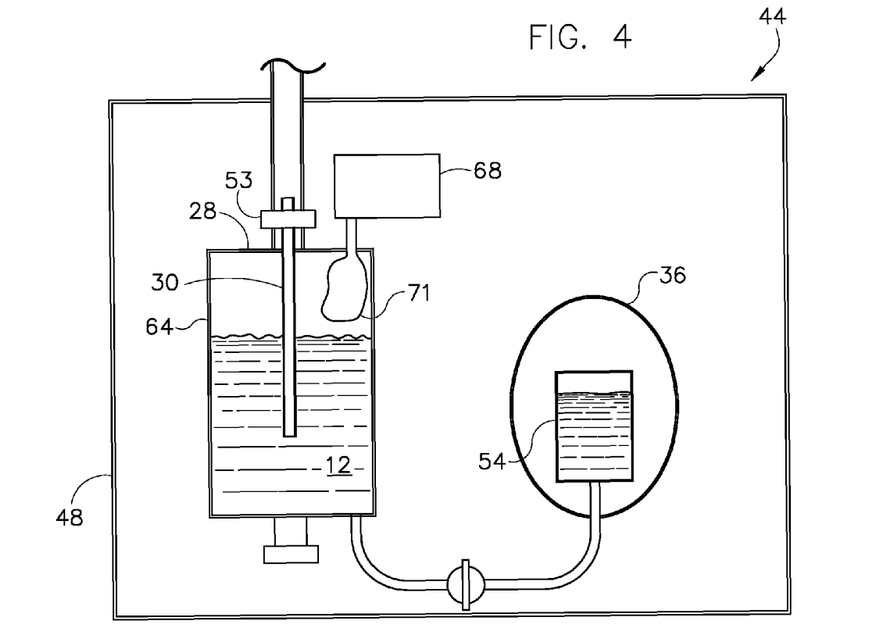
FIG. 4 is a cross-sectional view of a quality control system according to another embodiment of the current invention.

In another embodiment of receiver vessel 28, a flexible bladder is incorporated therein. As shown in FIG. 4, receiver vessel 28 is in the form of a rigid container 64 having an inflatable bladder 71 positioned therein, although it is also envisioned that a flexible container could also be implemented rather than rigid container 64. In order to inflate bladder 71, an automated displacement mechanism is attached thereto in the form of a pump 68. Pump 68 fills inflatable bladder 71 with a pressurized gas or liquid in order to increase the size of bladder 71 to occupy a greater volume in rigid container 64. As bladder 71 increases in size, pharmaceutical product 12 is forced out from out from receiver vessel 28 and into appendage 36. Such a configuration allows for the use of a fluid or gas to displace the product 12 without compromising the sterility of the quality control system 44. Additionally, the gas or fluid used to inflate bladder 71 may be maintained at a specific temperature and aid in modifying the temperature of pharmaceutical product 12 in receiver vessel 28. A closable/one-way valve 53 is also included in receiver vessel 28 and is positioned on nozzle 30 to prevent pharmaceutical product 12 from traveling back up the nozzle 30 when bladder 71 is inflated to displace pharmaceutical product 12.

Figure 5:
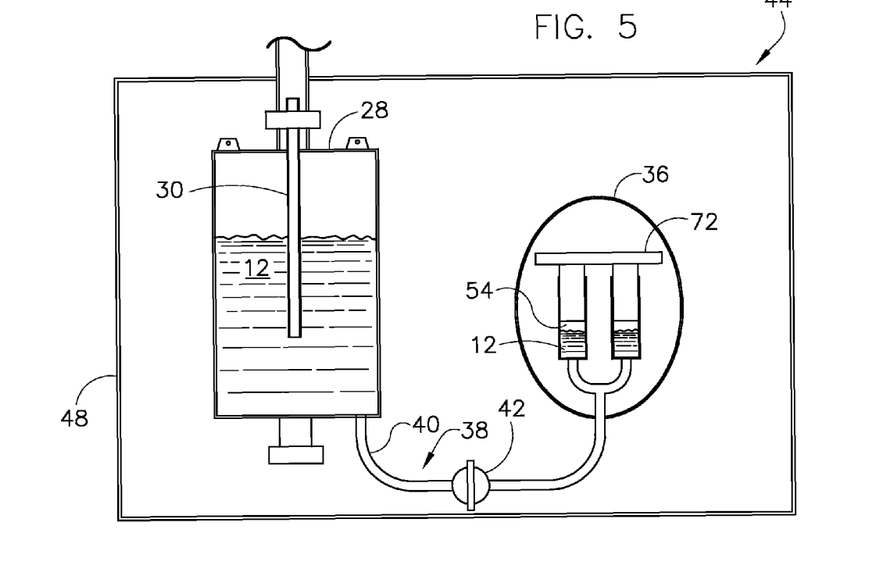
FIG. 5 is a cross-sectional view of a quality control system according to another embodiment of the current invention.

As shown in FIG. 5, in another embodiment of quality control system 44, appendage 36 includes therein a sliding plunger 72 (i.e., syringe) that functions as an automated displacement mechanism to draw-in pharmaceutical product 12 from receiver vessel 28. Sliding plunger 72 slides within chambers 54 to modify a volume therein. Thus, when it is desired to draw pharmaceutical product 12 into appendage 36, sliding plunger 72 can be adjusted to increase a volume in chamber 54, thereby lowering pressure in chamber 54 to create a pressure differential between the appendage 36 and receiver vessel 28 and drive a transfer of pharmaceutical product 12 to chambers 54.

Figure 6:
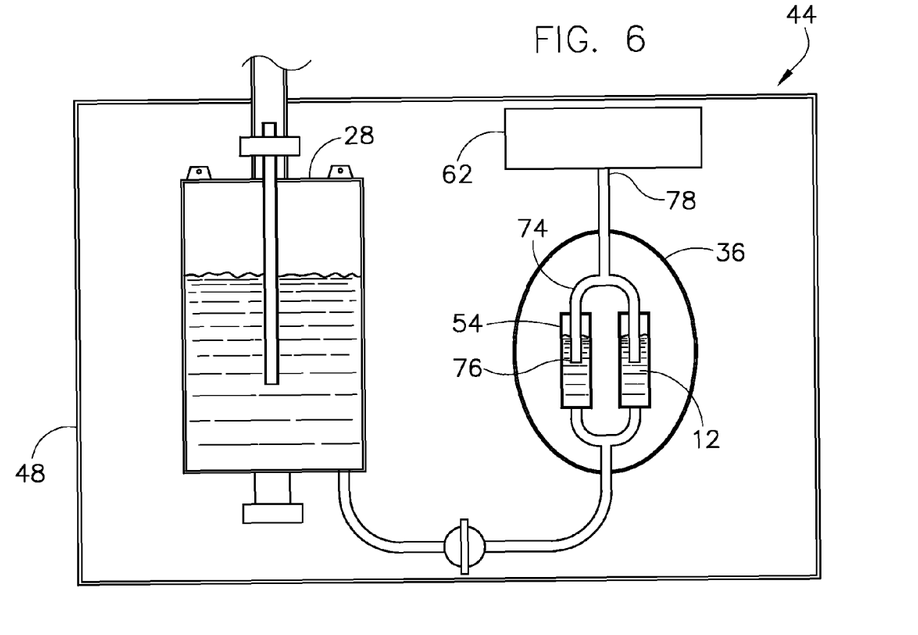
FIG. 6 is a cross-sectional view of a quality control system according to another embodiment of the current invention.
Figure 7:
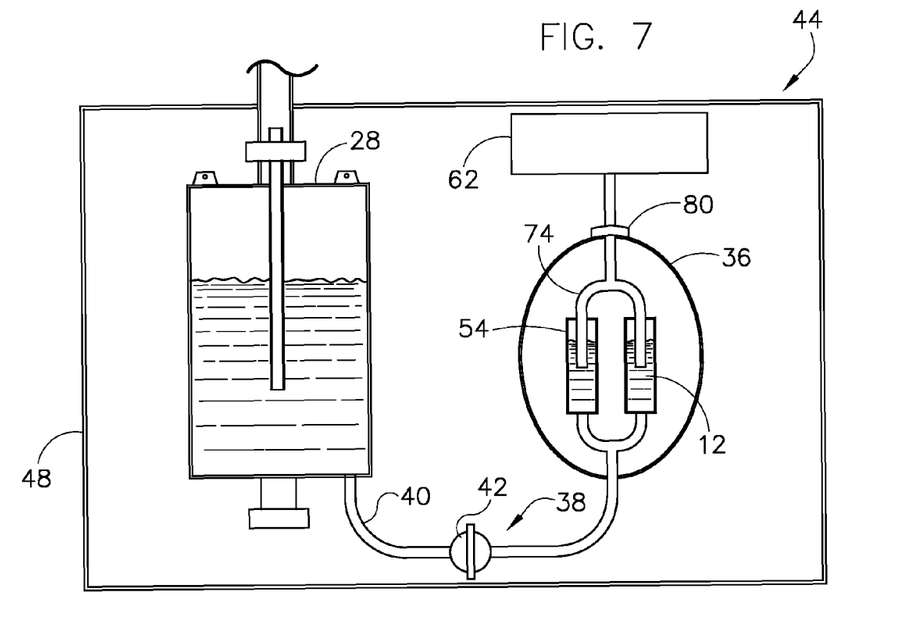
FIG. 7 is a cross-sectional view of a quality control system according to another embodiment of the current invention.
Figure 8:
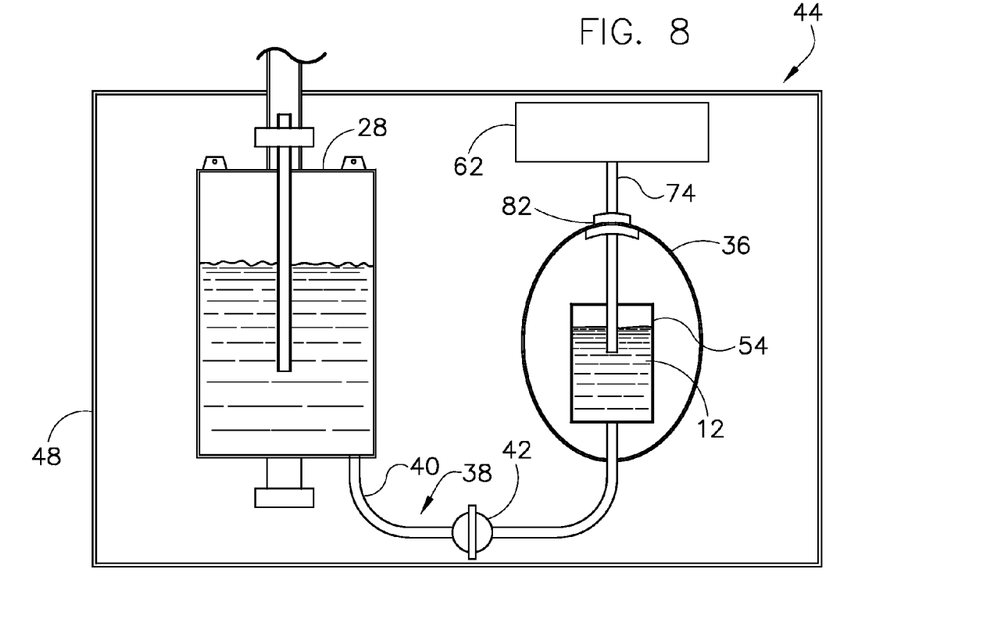
FIG. 8 is a cross-sectional view of a quality control system according to another embodiment of the current invention.

Referring now to FIG. 6, quality control system 44 is configured to perform contact based QC measurements on pharmaceutical product 12 that is displaced into appendage 36. In such a configuration, a probe 74 or other suitable sensing device is included within appendage 36 that is configured to measure one or more QC parameters of the pharmaceutical product 12. The probe is positioned such that a portion thereof extends into at least one of chambers 54 to be in contact with pharmaceutical product 12 therein. Probe 74 may be a standardized, off-the-shelf probe built into the appendage 36 such that one end 76 of the probe may directly contact the pharmaceutical product 12 while a data output end 78 may be electrically connected by the operator to the CPU 62. In another embodiment, and as shown in FIG. 7, the probe/sensor 74 may be incorporated into the design of appendage 36, such that the probe 74 is contained entirely within the appendage. In such a design, a data output connection 80 is made between appendage 36 and CPU 62. In yet another embodiment, and as shown in FIG. 8, probe 74 is a quality control device that is external to and separate from appendage 36. Appendage 36 is designed to accommodate insertion of probe 74 into chambers 54 and into contact with pharmaceutical product 12 by way of a connection 82. In any of the three embodiments described above, probe 74 is positioned to perform contact based QC measurements on pharmaceutical product 12 to determine safety and efficacy of the product.

Figure 9:
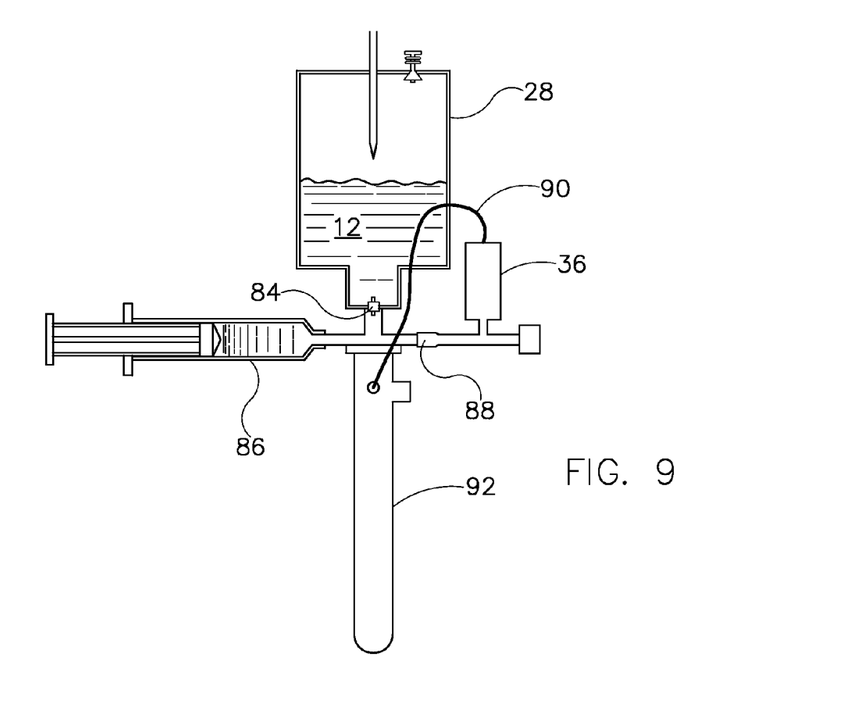
FIG. 9 is a cross-sectional view of a portion of a quality control system according to another embodiment of the current invention.

It is also envisioned that a number of appendages be included in quality control system 44 for performing QC measurements. Referring to FIG. 9, receiver vessel 28 includes a one-way valve 84 positioned at a bottom opening thereof. Pharmaceutical product 12 is drawn from receiver vessel 28 by way of a syringe 86 fluidly connected thereto. After pharmaceutical product 12 is drawn into syringe 86, the syringe is then depressed to force the product therefrom and through a second one-way valve 88 into appendage 36. Appendage 36 also includes a transfer tube 90 connected thereto that allows for pharmaceutical product 12 to flow from appendage 36 into a flask 92 (i.e., a second appendage). As such, separate QC analyses can be performed on pharmaceutical product 12 in each of appendage 36 and flask 92, which allows for multiple types of measurements to be taken.

While a number of automatic displacement mechanisms have been provided above for the transfer of pharmaceutical product from a receiver vessel to one or more appendages, it is also envisioned that other methods could be implemented.

For example, an appendage can be positioned below the receiver vessel such that transfer of a pharmaceutical product from the receiver vessel to the appendage is induced by gravity. That is, pharmaceutical product will automatically flow from the receiver vessel to the appendage due to gravitational forces and can be controlled by way of a one-way closeable sterile valve positioned within a sample tube connecting the receiver vessel and the appendage.

Therefore, according to one embodiment of the invention, a quality control system for measuring parameters in a pharmaceutical product includes a receiver vessel to receive a pharmaceutical product therein and a sample tube having a first end attached to the receiver vessel, the sample tube configured to remove pharmaceutical product from the receiver vessel. The quality control system also includes an appendage connected to a second end of the sample tube that has at least one chamber therein to receive a quantity of pharmaceutical product from the receiver vessel. A valve is positioned within the sample tube to control flow of the pharmaceutical product to the appendage and prevent flow of the pharmaceutical product from the appendage back into the receiver vessel. The quality control system further includes a quality control device configured to measure at least one parameter of the pharmaceutical product in at least one of the receiver vessel and the appendage.

In accordance with another embodiment of the invention, a sterile fluid path system includes a vial constructed to contain a solidified pharmaceutical sample therein, a container having a dissolution medium therein to dissolve the solidified pharmaceutical sample, and a tubing system connecting the vial and the container configured to transfer the dissolution medium into the vial and transfer a pharmaceutical product out of the vial, wherein the pharmaceutical product is comprised of the dissolved solidified pharmaceutical sample and the dissolution medium. The sterile fluid path system also includes a receiver vessel attached to the tubing system to receive the pharmaceutical product and an appendage fluidly connected to the receiver vessel and having one or more isolated sections therein to receive a quantity of the pharmaceutical product. The sterile fluid path system further includes a one-way valve and tube assembly positioned between the receiver vessel and the appendage to control flow of the pharmaceutical product to the appendage and a measurement apparatus configured to measure at least one parameter of the pharmaceutical product in the appendage.

In accordance with yet another embodiment of the invention, a method of constructing a quality control system for measuring parameters in a pharmaceutical product includes the steps of forming a receiver vessel configured to hold a liquid pharmaceutical product therein and fluidly connecting an appendage to the receiver vessel, the appendage having at least one chamber therein to receive the pharmaceutical product transferred thereto from the receiver vessel. The method also includes the steps of connecting a sample path to the receiver vessel and the appendage, positioning a one-way sterile valve in a sample path to control flow of the pharmaceutical product, and positioning a quality control device in proximity to the receiver vessel and the appendage to perform quality control measurements on the pharmaceutical product.

The present invention has been described in terms of the preferred embodiment, and it is recognized that equivalents, alternatives, and modifications, aside from those expressly stated, are possible and within the scope of the appending claims.

What is claimed is:

1. A disposable device for maintaining sterility of a hyperpolarized pharmaceutical product during quality control analysis of the product comprising:
   a receiver vessel to receive a sterile hyperpolarized pharmaceutical product therein;
   a sample tube having a first end attached to the receiver vessel, the sample tube configured to remove the hyperpolarized pharmaceutical product from the receiver vessel;
   an appendage connected to a second end of the sample tube, the appendage having at least one chamber therein to receive a quantity of pharmaceutical product from the receiver vessel while maintaining sterility of the hyperpolarized pharmaceutical product; and
   a one-way sterile valve positioned within the sample tube to control flow of the hyperpolarized pharmaceutical product to the appendage and prevent flow of the hyperpolarized pharmaceutical product from the appendage back into the receiver vessel;
   an automated displacement mechanism directly attached to the receiver vessel and configured to apply pressure to said receiver vessel to allow displacement of the hyperpolarized pharmaceutical product from said receiver vessel into the appendage; and
   wherein the disposable device is comprised of a material that is non-reactive to the hyperpolarized pharmaceutical product.

2. The disposable device of claim 1 wherein the automated displacement mechanism further comprises a sliding plunger positioned in the at least one chamber and configured to modify a volume and a pressure therein.

3. The disposable device of claim 1 wherein the receiver vessel further comprises a flexible container and wherein the automated displacement mechanism is further configured to apply a pressure to the flexible container to displace the hyperpolarized pharmaceutical product therefrom.

4. The disposable device of claim 1 wherein the receiver vessel further comprises a rigid container having an inflatable bladder therein and wherein the automated displacement mechanism is further configured to inflate the inflatable bladder to displace the hyperpolarized pharmaceutical product from the receiver vessel.

5. The disposable device of claim 1 wherein the at least one chamber includes a plurality of path-lengths therein to allow for optical measurements of the hyperpolarized pharmaceutical product.

6. The disposable device of claim 1 wherein the at least one chamber further comprises a chemical reagent contained therein that measurably reacts with the hyperpolarized pharmaceutical product.

7. The disposable device of claim 1 further comprising a probe configured to measure the at least one parameter of the hyperpolarized pharmaceutical product, wherein the probe is built into the appendage and includes a first end in direct contact with the hyperpolarized pharmaceutical product and a second end connected to the quality control device.

8. The disposable device of claim 1 wherein the appendage further comprises a probe incorporated therein configured to measure the at least one parameter of the hyperpolarized pharmaceutical product.

9. The disposable device of claim 1 wherein the quality control device further comprises a probe configured to measure the at least one parameter of the hyperpolarized pharmaceutical product.

10. The disposable device of claim 1 wherein the at least one parameter includes at least one of temperature, pH level, mass, volume, liquid state polarization, and concentration.

11. The disposable device of claim 1 wherein the receiver vessel further comprises a nozzle extending into an interior volume of the receiver vessel, the nozzle configured to mix the hyperpolarized pharmaceutical product entering the receiver vessel.

12. The disposable device of claim 1 wherein the quality control device further comprises an infrared pyrometer to perform optical temperature measurements of the hyperpolarized pharmaceutical product.

13. The disposable device of claim 1 wherein the receiver vessel includes at least one wall having a low thermal mass, the at least one wall configured to allow for optical measurements by way of the infrared pyrometer.

14. The disposable device of claim 1 wherein the quality control device further comprises a fiber optics based spectrometer system configured to optically measure the at least one parameter of the hyperpolarized pharmaceutical product.

15. The disposable device of claim 1 wherein the appendage is comprised of a material configured to allow for optical measurements on the hyperpolarized pharmaceutical product contained therein.

16. The disposable device of claim 1 further comprising a flask fluidly connected to the appendage to receive the hyperpolarized pharmaceutical product therefrom.

* * * * *